United States Patent

Kroin et al.

[11] Patent Number: 6,025,359
[45] Date of Patent: *Feb. 15, 2000

[54] DRUG RESISTANCE AND MULTIDRUG RESISTANCE MODULATORS

[75] Inventors: Julian Stanley Kroin; Bryan Hurst Norman, both of Indianapolis, Ind.

[73] Assignee: Eli Lilly and Company, Indianapolis, Ind.

[*] Notice: This patent issued on a continued prosecution application filed under 37 CFR 1.53(d), and is subject to the twenty year patent term provisions of 35 U.S.C. 154(a)(2).

This patent is subject to a terminal disclaimer.

[21] Appl. No.: 08/873,782

[22] Filed: Jun. 12, 1997

Related U.S. Application Data

[60] Provisional application No. 60/020,807, Jun. 17, 1996.

[51] Int. Cl.$^7$ .................... A61K 31/495; C07D 295/088
[52] U.S. Cl. .......................................... 514/255; 544/381
[58] Field of Search .............................. 544/381; 514/255

[56] References Cited

U.S. PATENT DOCUMENTS

| | | | |
|---|---|---|---|
| 5,112,817 | 5/1992 | Fukazawa et al. | 514/183 |
| 5,523,304 | 6/1996 | Sunkara | 514/277 |
| 5,596,002 | 1/1997 | Hofheinz et al. | 514/313 |
| 5,654,304 | 8/1997 | Pfister et al. | 514/253 |
| 5,776,939 | 7/1998 | Kroin et al. | 514/255 |

FOREIGN PATENT DOCUMENTS

| | | |
|---|---|---|
| WO93/17021 | 9/1993 | WIPO . |
| WO94/22842 | 10/1994 | WIPO . |
| WO94/24107 | 10/1994 | WIPO . |

OTHER PUBLICATIONS

Bellamy et al, *Cancer Investigation* 8 (5) p. 547–562, 1990.

Ruetz, Stephan, et al., "The pfmdrl gene of *Plasmodium falciparum* confers cellular resistance to antimalarial drugs in yeast cells," *Proc. Natl. Acad. Sci. USA*, vol. 93, pp. 9942–9947, (1996).

Terao, Toshimitsu, et al., "Active Secretion of Drugs from the Small Intestinal Epithelium in Rats by P–Glycoprotein Functioning as an Absorption Barrier," *J. Pharm. Pharmacol*, 48:1083–1089 (1996).

Pfister, J. R., et al., "Methanodibenzosuberylpiperazines as Potent Multidrug Resistance Reversal Agents," *Bioorganic & Medicinal Chemistry Letters*, vol. 5, No. 21, pp. 2473–2476 (1995).

Patel et al., Investigational NewDrugs,12, pp.1–13, 1994.

Slate et al., In Vivo, 7, pp.519–524, 1993.

Slate et al., Cancer Research,15, pp.811–814, 1995.

Hunter et al., Pharmaceutical Research,10, pp.743–749, 1993.

Medicinal Chemistry (2nd Ed.) by Alfred Burger, pp. 72–78, 1960.

*Primary Examiner*—Emily Bernhardt
*Attorney, Agent, or Firm*—Elizabeth A. Dawalt; Brian P. Barrett; Robert A. Conrad

[57] ABSTRACT

Drug and multidrug resistant modulators of the formula:

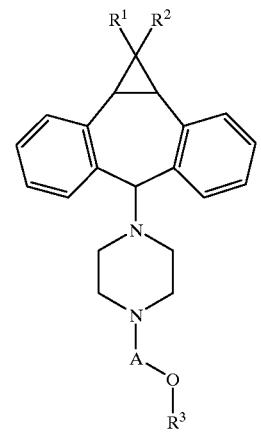

where $R^1$ and $R^2$ are independently hydrogen or halo; A is —$CH_2$—$CH_2$—, —$CH_2$—$CHR^4$—$CH_2$—, or —$CH_2$—$CHR^5$—$CHR^6$—$CH_2$—, where $R^4$ is —H, —OH, or acyloxy; one of $R^5$ or $R^6$ is —H, —OH, or acyloxy, and the other is —H; $R^3$ is a polyaryl; and pharmaceutically acceptable salts and solvates thereof, are described and claimed. Use of the new compounds in the preparation of pharmaceutical compositions is described and claimed. In addition, methods for treating drug and multidrug resistance in various diseases using a compound, or pharmaceutically acceptable salt or solvate thereof, of this invention are described and claimed. Also, methods of enhancing oral bioavailability of a drug and methods of enhancing bioavailability of a drug to the brain using a compound, or pharmaceutically acceptable salt or solvate thereof, of this invention are described and claimed.

6 Claims, No Drawings

DRUG RESISTANCE AND MULTIDRUG RESISTANCE MODULATORS

This application claims the benefit of U.S. Provisional Application No. 60/020,807 filed Jun. 17, 1996.

FIELD OF THE INVENTION

This invention relates to the field of synthetic organic chemistry. Specifically, the invention relates to pharmaceutical compounds that are useful in the field of drug resistance and multidrug resistance.

BACKGROUND OF THE INVENTION

Among the problems faced in certain types of drug therapy, including cancer chemotherapy and malaria drug therapy, are the phenomena of resistance to treatment regimens. The resistance means, for example, that cancerous tumors that have responded well initially to a particular drug or drugs, later develop a tolerance to the drug(s) and cease responding. Drug resistance is the name given to the circumstance when a disease (e.g., malaria or cancer) does not respond to a treatment drug or drugs. Drug resistance can be either intrinsic, which means the disease has never been responsive to the drug or drugs, or it can be acquired, which means the disease ceases responding to a drug or drugs that the disease had previously been responsive to. Multidrug resistance is a specific type of drug resistance that is characterized by cross-resistance of a disease to more than one functionally and/or structurally unrelated drugs. Multidrug resistance in the field of cancer, is discussed in greater detail in "Detoxification Mechanisms and Tumor Cell Resistance to Anticancer Drugs," by Kuzmich and Tew, particularly section VII "The Multidrug-Resistant Phenotype (MDR)," *Medical Research Reviews*, Vol. 11, No. 2, 185–217, (Section VII is at pp. 208–213) (1991); and in "Multidrug Resistance and Chemosensitization: Therapeutic Implications for Cancer Chemotherapy," by Georges, Sharom and Ling, *Advances in Pharmacology*, Vol. 21, 185–220 (1990).

Treatment of drug and multidrug resistance typically involves the coadministration of a drug suitable for treatment of the disease and a compound known as a drug resistance modulator or a multidrug resistance modulator. Drug and multidrug resistance modulators act through various mechanisms to cause a drug or drugs suitable for treatment of a disease to begin and/or continue to function as a therapeutic agent.

One known mechanism by which certain drug and multidrug resistance modulators function is by their interaction with a protein that is variously called Multidrug-Resistance 1 protein (MDR1), Pleiotropic-glycoprotein (P-glycoprotein), Pgp or P170, referred to herein as "P-glycoprotein". P-glycoprotein is endogenous in cell membranes, including certain drug resistant cells, multidrug resistant tumor cells, gastrointestinal tract cells, and the endothelial cells that form the blood brain barrier. P-glycoprotein acts as an efflux pump for the cell. Certain substances, undesirably including treatment drugs for various diseases, are pumped out of the cell by the P-glycoprotein prior to their having an effect on the cell. Drug and multidrug resistance modulators interact with P-glycoprotein. This interaction interferes with the P-glycoprotein "drug efflux pump" action thereby permitting the treatment drug to enter and remain in the cell and have its intended effect.

In addition to inhibiting the efflux of various drugs from tumor cells, drug and multidrug resistance modulators that interact with P-glycoprotein also function to enhance oral bioavailability of nutrients or drugs, that are affected by the action of P-glycoprotein, through the gastrointestinal tract. Oral bioavailability refers to the ability of a drug that is administered orally to be transported across the gastrointestinal tract and enter into the bloodstream. A drug or multidrug resistance modulator that interacts with P-glycoprotein should enhance the oral bioavailability of a drug or nutrient by interfering with the efflux pump action of P-glycoprotein.

P-glycoprotein is believed to be present on both sides of the endothelial cell layer of the capillary tube of the brain. It is this capillary tube that functions physiologically as the blood-brain barrier. The blood brain barrier is believed to restrict the entry of many different types of compounds, including drugs whose site of action is within the brain, from entering the brain. Certain drug and multidrug resistance modulators that interact with P-glycoprotein also can function to enhance bioavailability of a drug to the brain by interacting with P-glycoprotein and thus interfering with the drug efflux pump action of P-glycoprotein on the treatment drug. This interference permits more of the treatment drug to cross the blood-brain barrier into the brain and remain there.

Certain drug or multidrug resistance modulators that interact with P-glycoprotein are known. They include: verapamil (a calcium channel blocker that lowers blood pressure and has also been found effective in vitro for treating drug-resistant malaria), certain steroids, trifluoroperazine (a central nervous system agent), vindoline, and reserpine (an α-2 blocker with central nervous system properties).

U.S. Pat. No. 5,112,817 to Fukazawa et al. discloses certain quinoline derivatives useful for the treatment of multidrug resistance in cancer. One of the initially promising active agents, MS-073, was found to be active in in vitro testing. However, MS-073 was found to have poor oral bioavailability and to suffer from instability problems in solution. Other compounds in the series, such as the biphenylmethylcarbonyl derivative MS-209, have been found to have better stability and oral bioavailability, but require the administration of higher doses to be effective as a multidrug resistance modulator.

PCT Pat. Application WO 94/24107 discloses 10,11-cyclopropyldibenzosuberane derivatives which are described as being useful as multidrug resistance modulators.

There remains a need to discover compounds that will interact with P-glycoprotein so that they will act as drug and multidrug resistance modulators to treat drug and multidrug resistance in various diseases. Additional compounds that interact with P-glycoprotein are also needed to act to enhance bioavailability of a drug or drugs to the brain and/or to act to enhance oral bioavailability of a drug or drugs.

SUMMARY OF THE INVENTION

The present invention provides compounds of Formula (A):

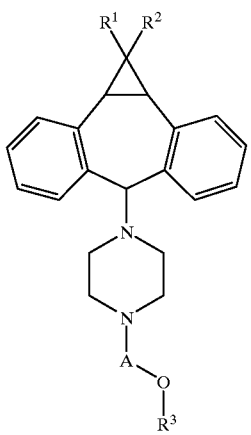

(A)

where $R^1$ and $R^2$ are independently hydrogen or halo; A is —$CH_2$—$CH_2$—, —$CH_2$—$CHR^4$—$CH_2$—, or —$CH_2$—$CHR^5$—$CHR^6$—$CH_2$—, where $R^4$ is —H, —OH, or acyloxy; one of $R^5$ and $R^6$ is —H, —OH, or acyloxy and the other is —H; and $R^3$ is a polyaryl; and pharmaceutically acceptable salts and solvates thereof.

The present invention also provides pharmaceutical compositions comprising a compound or pharmaceutically acceptable salt or solvate thereof of Formula (A) in association with a pharmaceutically acceptable carrier, diluent, or excipient.

The present invention further provides a method of treatment for a drug resistant disease comprising coadministering to a mammal in need thereof a resistance modulating amount of a compound or salt or solvate thereof of Formula (A) and an effective amount of a treatment drug for said drug resistant disease.

The present invention further provides a method of treatment for a multidrug resistant disease comprising coadministering to a mammal in need thereof a multidrug resistance modulating amount of a compound or salt or solvate thereof of Formula (A) and an effective amount of a treatment drug for said multidrug resistant disease.

The present invention further provides a method for enhancing bioavailability of a drug to the brain, comprising coadministering to a mammal in need thereof a therapeutically effective amount of said drug and an amount of a compound or salt or solvate thereof of Formula (A) sufficient to allow said drug to cross the blood-brain barrier and enter the brain.

The present invention further provides a method for enhancing oral bioavailability of a drug comprising administering to a mammal in need thereof a therapeutically effective amount of said drug and an amount of a compound or salt or solvate thereof of Formula (A) sufficient to allow said drug to be transported across the gastrointestinal tract and enter the bloodstream.

DETAILED DESCRIPTION OF THE INVENTION

The following definitions are set forth to illustrate and define the meaning and scope of the various terms used to describe the invention herein.

The term "alkyl" refers to a fully saturated monovalent radical having the stated number of carbon atoms containing only carbon and hydrogen, and which may be a cyclic, polycyclic, branched or straight chain radical. This term is exemplified by radicals containing from 1–6 carbon atoms, such as, but not limited to, methyl, ethyl, propyl, t-butyl, pentyl, neopentyl, hexyl, and cyclohexyl. "Lower alkyl" refers to alkyl radicals of from 1–4 carbon atoms.

The term "acyloxy" refers to the group —O—C(O)—$R^7$ where $R^7$ is $C_1$–$C_6$ alkyl.

"Polyaryl" refers to monovalent fused ring systems that contain at least two, and at most four fused aromatic rings. All the aromatic rings in these systems may optionally be substituted, with the proviso that only one to three of the hydrogens on each ring may be replaced.

The term "aromatic" refers to rings containing one or more groups of atoms in a cyclic array that contains clouds of delocalized π electrons above and below the plane of the atoms; furthermore, the π clouds must contain a total of (4q+2) π electrons, where q is any positive integer. For purposes of this application "aromatic rings" are defined as unsaturated carbocyclic rings which can optionally be substituted. Aromatic rings can contain any number of carbon atoms, as long as they retain their aromatic character and are sterically feasible. The preferred ring size is a six carbon ring.

The term "substituted" means one to three hydrogens on the structure have been replaced with one to three moieties independently selected from the group consisting of bromo, chloro, iodo, fluoro, $C_{1-C_6}$ alkyl, —COOH, amino, cyano, nitro, trifluoromethyl, difluoromethoxy, and hydroxyl groups, with the proviso that any substituted structure must be so configured that it is sterically feasible, affords a stable structure and is capable of reacting as described herein.

Examples of polyaryl ring systems used in the present invention include, but are not limited to, naphthyl, phenanthryl, anthryl, triphenylenyl, and chrysylenyl. Representative formulae for some of these polyaryl ring systems include:

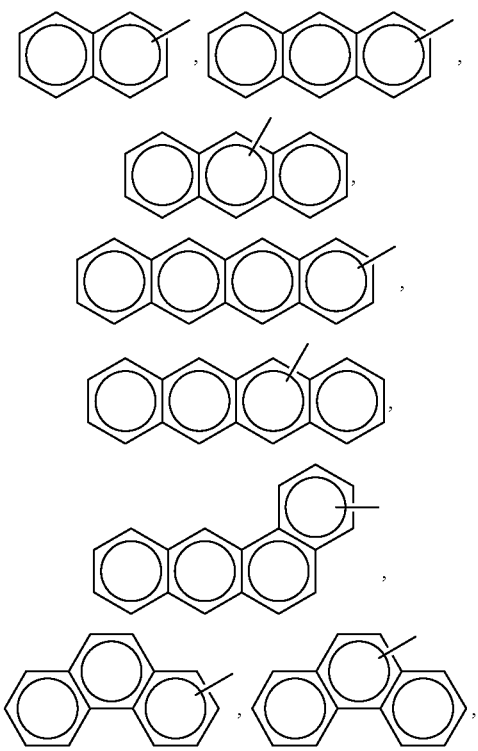

-continued

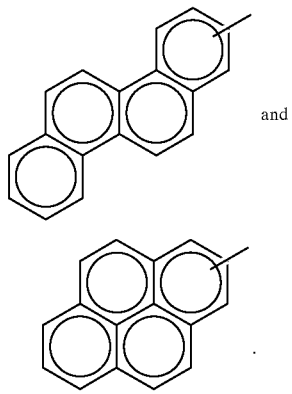

and

The term "carbocyclic" refers to a ring structure which has only carbon atoms in the ring.

The term "halo" refers to fluoro, bromo, chloro and iodo.

A "pharmaceutically acceptable salt" may be any non-toxic salt derived from an inorganic or organic acid that is suitable for administration as a drug. The salts are derived from inorganic acids, such as hydrochloric acid, hydrobromic acid, sulfuric acid (giving the sulfate and bisulfate as acetic salts), nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, salicylic acid, p-toluenesulfonic acid, hexanoic acid, heptanoic acid, cyclopentanepropionic acid, lactic acid, o-(4-hydroxy-benzoyl) benzoic acid, 1,2-ethanedisulfonic acid, 2-hydroxyethanesulfonic acid, benzenesulfonic acid, p-chlorobenzenesulfonic acid, 2-naphthalenesulfonic acid, camphorsulfonic acid, 4-methylbicyclo[2.2.2]oct-2-ene-1-carboxylic acid, glucoheptonic acid, 4,4'-methylenebis(3-hydroxy-2-naphthoic) acid, 3-phenylpropionic acid, trimethylacetic acid, t-butylacetic acid, laurylsulfuric acid, glucuronic acid, glutamic acid, 3-hydroxy-2-naphthoic acid, stearic acid, muconic acid and the like.

A "pharmaceutically acceptable solvate" refers to a form of a compound that has clusters of solvent molecules clinging to the molecules of the compound and which form is suitable for administration as a drug. The solvent may be water or any common organic solvent.

The term "bioavailability" refers to the degree and rate at which a drug, or other substance, becomes available to a target tissue within a mammal.

The term "treatment" or "treating" means administering an appropriate therapeutic or prophylactic amount of a compound to a mammal.

The term "effective amount" means a dosage sufficient to cause a positive change in the disease state being treated. The term "positive change" will vary in meaning depending on the patient, the disease and the treatment being undergone. For example, an effective amount of an oncolytic can be an amount that causes a reduction in the size of a cancerous tumor, or where no reduction in tumor size occurs, an effective amount of an oncolytic could be that amount that causes a decrease in analgesic consumption for the patient suffering from cancer. The term "coadministering" means a disease treatment drug and a compound of Formula (A), or a pharmaceutically acceptable salt or solvate thereof, are given to a mammal. The drug and the compound of Formula (A) or a pharmaceutically acceptable salt or solvate thereof, are given to a mammal simultaneously or at different times.

The term "drug resistance" refers to the circumstance when a disease does not respond to a treatment drug or drugs. Drug resistance can be either intrinsic, which means the disease has never been responsive to the drug or drugs, or it can be acquired, which means the disease ceases responding to a drug or drugs that the disease had previously responded to.

"Multidrug resistance" means a specific type of drug resistance characterized by cross-resistance of a disease to more than one functionally and/or structurally unrelated drugs. Multidrug resistance can be either intrinsic or acquired.

Compounds of the claimed invention are compounds of Formula (A):

(A)

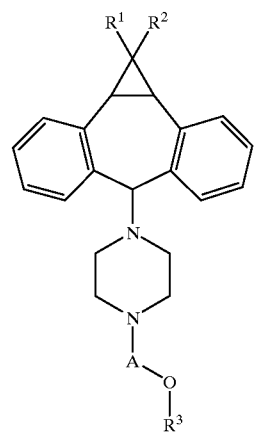

where $R^1$ and $R^2$ are independently hydrogen or halo; A is —$CH_2$—$_{CH2}$—, —$CH_2$—$_{CHR}^4$—$CH_2$—, or —$CH_2$—$CHR^5$—$CHR^6$—$CH_2$—, where $R^4$ is —H, —OH, or acyloxy; one of $R^5$ and $R^6$ is —H, —OH, or acyloxy and the other is —H; and $R^3$ is a polyaryl; and pharmaceutically acceptable salts and solvates thereof.

The compounds of Formula (A) exist in two isomeric configurations defined by the relationship of the 10,11-cyclopropyl and the 5-piperazinyl substituents on the dibenzosuberane. When the 10,11-cyclopropyl and the 5-piperazinyl substituents are both oriented in the same direction vis-a-vis the dibenzosuberane (e.g., both up or both down) the isomeric form is called "syn." When the 10,11-cyclopropyl and the 5-piperazinyl substituents are oriented in opposite directions vis-a-vis the dibenzosuberane (e.g., one up and the other down) the isomeric form is called "anti." In general, the drug/multidrug resistance activity of the compounds of Formula (A) in the "anti" configuration has been found to be far superior to the activity of the compounds of Formula (A) in the "syn" configuration.

Certain compounds of Formula (A) will have an asymmetric center within the "A" substituent when $R^4$ is not hydrogen or at whichever one of $R^5$ and $R^6$ is not hydrogen. These compounds can exist in two stereochemical forms, called (+) and (−) or called (R)- and (S)-, or as mixtures of the two sterioisomers. The (R)- and (S)-designation will be used in this application.

While specific stereoisomers are disclosed and named, the present invention is to be interpreted to include both the "anti" and "syn" configurations, the individual (R)-and (S)-stereoisomers within those configurations, as well as mixtures, racemic and otherwise, thereof.

Preferred compounds of the claimed invention include:

(2R)-anti-1-{3-[4-(10,11-difluorocyclopropyldibenzosuber-5-yl)piperazin-1-yl]-2-hydroxypropoxy}naphthalene, or a pharmaceutically acceptable salt or solvate thereof, (2R)-anti-1-{3-[4-(10,11-difluorocyclopropyldibenzosuber-5-yl)piperazin-1-yl]-2-hydroxypropoxy}phenanthrene, or a pharmaceutically acceptable salt or solvate thereof, (2R)-anti-1-{3-[4-(10,11-difluorocyclopropyldibenzosuber-5-yl)piperazin-1-yl]-2-hydroxypropoxy}anthracene, or a pharmaceutically acceptable salt or solvate thereof, (2R)-anti-1-{3-[4-(10,11-difluorocyclopropyldibenzosuber-5-yl)piperazin-1-yl]-2-hydroxypropoxy}triphenylene, or a pharmaceutically acceptable salt or solvate thereof, (2R)-anti-1-{3-[4-(10,11-difluorocyclopropyldibenzosuber-5-yl)piperazin-1-yl]-2-hydroxypropoxy}chrysene, or a pharmaceutically acceptable salt or solvate thereof, (2R)-syn-1-{3-[4-(10,11-difluorocyclopropyldibenzosuber-5-yl)piperazin-1-yl]-2-hydroxypropoxy}naphthalene, or a pharmaceutically acceptable salt or solvate thereof, (2R)-syn-1-{3-[4-(10,11-difluorocyclopropyldibenzosuber-5-yl)piperazin-1-yl]-2-hydroxypropoxy}phenanthrene, or a pharmaceutically acceptable salt or solvate thereof, (2R)-syn-1-{3-[4-(10,11-difluorocyclopropyldibenzosuber-5-yl)piperazin-1-yl]-2-hydroxypropoxy}anthracene, or a pharmaceutically acceptable salt or solvate thereof, (2R)-syn-1-{3-[4-(10,11-difluorocyclopropyldibenzosuber-5-yl)piperazin-1-yl]-2-hydroxypropoxy}triphenylene, or a pharmaceutically acceptable salt or solvate thereof, (2R)-syn-1-{3-[4-(10,11-difluorocyclopropyldibenzosuber-5-yl)piperazin-1-yl]-2-hydroxypropoxy}chrysene, or a pharmaceutically acceptable salt or solvate thereof, (2R)-anti-1-{4-[4-(10,11-difluorocyclopropyldibenzosuber-5-yl)piperazin-1-yl]-2-hydroxybutoxy}naphthalene, or a pharmaceutically acceptable salt or solvate thereof, (2R)-anti-1-{4-[4-(10,11-difluorocyclopropyldibenzosuber-5-yl)piperazin-1-yl]-2-hydroxybutoxy}phenanthrene, or a pharmaceutically acceptable salt or solvate thereof, (2R)-anti-1-{4-[4-(10,11-difluorocyclopropyldibenzosuber-5-yl)piperazin-1-yl]-2-hydroxybutoxy}anthracene, or a pharmaceutically acceptable salt or solvate thereof, (2R)-anti-1-{4-[4-(10,11-difluorocyclopropyldibenzosuber-5-yl)piperazin-1-yl]-2-hydroxybutoxy}triphenylene, or a pharmaceutically acceptable salt or solvate thereof, (2R)-anti-1-{4-[4-(10,11-difluorocyclopropyldibenzosuber-5-yl)piperazin-1-yl]-2-hydroxybutoxy}chrysene, or a pharmaceutically acceptable salt or solvate thereof, (2R)-anti-1-{4-[4-(10,11-difluorocyclopropyldibenzosuber-5-yl)piperazin-1-yl]-3-hydroxybutoxy}naphthalene, or a pharmaceutically acceptable salt or solvate thereof, (2R)-anti-1-{4-[4-(10,11-difluorocyclopropyldibenzosuber-5-yl)piperazin-1-yl]-3-hydroxybutoxy}phenanthrene, or a pharmaceutically acceptable salt or solvate thereof, (2R)-anti-1-{4-[4-(10,11-difluorocyclopropyldibenzosuber-5-yl)piperazin-1-yl]-3-hydroxybutoxy}anthracene, or a pharmaceutically acceptable salt or solvate thereof, (2R)-anti-1-{4-[4-(10,11-difluorocyclopropyldibenzosuber-5-yl)piperazin-1-yl]-3-hydroxybutoxy}triphenylene, or a pharmaceutically acceptable salt or solvate thereof, (2R)-anti-1-{4-[4-(10,11-difluorocyclopropyldibenzosuber-5-yl)piperazin-1-yl]-3-hydroxybutoxy}chrysene, or a pharmaceutically acceptable salt or solvate thereof, (2R)-anti-1-{3-[4-(10,11-cyclopropyldibenzosuber-5-yl)piperazin-1-yl]-2-hydroxypropoxy}naphthalene, or a pharmaceutically acceptable salt or solvate thereof, (2R)-anti-1-{3-[4-(10,11-cyclopropyldibenzosuber-5-yl)piperazin-1-yl]-2-hydroxypropoxy}phenanthrene, or a pharmaceutically acceptable salt or solvate thereof, (2R)-anti-1-{3-[4-(10,11-cyclopropyldibenzosuber-5-yl)piperazin-1-yl]-2-hydroxypropoxy}anthracene, or a pharmaceutically acceptable salt or solvate thereof, (2R)-anti-1-{3-[4-(10,11-cyclopropyldibenzosuber-5-yl)piperazin-1-yl]-2-hydroxypropoxy}triphenylene, or a pharmaceutically acceptable salt or solvate thereof, (2R)-anti-1-{3-[4-(10,11-cyclopropyldibenzosuber-5-yl)piperazin-1-yl]-2-hydroxypropoxy}chrysene, or a pharmaceutically acceptable salt or solvate thereof, (2R)-anti-1-{3-[4-(10,11-fluorocyclopropyldibenzosuber-5-yl)piperazin-1-yl]-2-hydroxypropoxy}naphthalene, or a pharmaceutically acceptable salt or solvate thereof, (2R)-anti-1-{3-[4-(10,11-fluorocyclopropyldibenzosuber-5-yl)piperazin-1-yl]-2-hydroxypropoxy}phenanthrene, or a pharmaceutically acceptable salt or solvate thereof, (2R)-anti-1-{3-[4-(10,11-fluorocyclopropyldibenzosuber-5-yl)piperazin-1-yl]-2-hydroxypropoxy}anthracene, or a pharmaceutically acceptable salt or solvate thereof, (2R)-anti-1-{3-[4-(10,11-fluorocyclopropyldibenzosuber-5-yl)piperazin-1-yl]-2-hydroxypropoxy}triphenylene, or a pharmaceutically acceptable salt or solvate thereof, (2R)-anti-1-{3-[4-(10,11-fluorocyclopropyldibenzosuber-5-yl)piperazin-1-yl]-2-hydroxypropoxy}chrysene, or a pharmaceutically acceptable salt or solvate thereof, anti-1-{2-[4-(10,11-cyclopropyldibenzosuber-5-yl)piperazin-1-yl]ethoxy}naphthalene, or a pharmaceutically acceptable salt or solvate thereof, anti-1-{2-[4-(10,11-cyclopropyldibenzosuber-5-yl)piperazin-1-yl]ethoxy}phenanthrene, or a pharmaceutically acceptable salt or solvate thereof, anti-1-{2-[4-(10,11-cyclopropyldibenzosuber-5-yl)piperazin-1-yl]ethoxy}anthracene, or a pharmaceutically acceptable salt or solvate thereof, anti-1-{2-[4-(10,11-cyclopropyldibenzosuber-5-yl)piperazin-1-yl]ethoxy}triphenylene, or a pharmaceutically acceptable salt or solvate thereof, anti-1-{2-[4-(10,11-cyclopropyldibenzosuber-5-yl)piperazin-1-yl]ethoxy}chrysene, or a pharmaceutically acceptable salt or solvate thereof, (2R)-anti-2-{3-[4-(10,11-difluorocyclopropyldibenzosuber-5-yl)piperazin-1-yl]-2-hydroxypropoxy}naphthalene, or a pharmaceutically acceptable salt or solvate thereof, (2R)-anti-2-{3-[4-(10,11-difluorocyclopropyldibenzosuber-5-yl)piperazin-1-yl]-2-hydroxypropoxy}phenanthrene, or a pharmaceutically acceptable salt or solvate thereof, (2R)-anti-2-{3-[4-(10,11-difluorocyclopropyldibenzosuber-5-yl)piperazin-1-yl]-2-hydroxypropoxy}anthracene, or a pharmaceutically acceptable salt or solvate thereof, (2R)-anti-2-{3-[4-(10,11-difluorocyclopropyldibenzosuber-5-yl)piperazin-1-yl]-2-hydroxypropoxy}triphenylene, or a pharmaceutically acceptable salt or solvate thereof, (2R)-anti-2-{3-[4-(10,11-difluorocyclopropyldibenzosuber-5-yl)piperazin-1-yl]-2-hydroxypropoxy}chrysene, or a pharmaceutically acceptable salt or solvate thereof, (2S)-anti-1-{3-[4-(10,11-difluorocyclopropyldibenzosuber-5-yl)piperazin-1-yl]-2-hydroxypropoxy}naphthalene, or a pharmaceutically acceptable salt or solvate thereof, (2S)-anti-1-{3-[4-(10,11-difluorocyclopropyldibenzosuber-5-yl)piperazin-1-yl]-2-hydroxypropoxy}phenanthrene, or a pharmaceutically acceptable salt or solvate thereof, (2S)-anti-1-{3-[4-(10,11-difluorocyclopropyldibenzosuber-5-yl)piperazin-1-yl]-2-hydroxypropoxy}anthracene, or a pharmaceutically acceptable salt or solvate thereof, (2S)-anti-1-{3-[4-(10,11-difluorocyclopropyldibenzosuber-5-yl)piperazin-1-yl]-2-hydroxypropoxy}triphenylene, or a pharmaceutically acceptable salt or solvate thereof, (2S)-anti-1-{3-[4-(10,11-difluorocyclopropyldibenzosuber-5-yl)piperazin-1-yl]-2-hydroxypropoxy}chrysene, or a pharmaceutically acceptable salt or solvate thereof, (2S)-anti-1-{4-[4-(10,11-difluorocyclopropyldibenzosuber-5-yl)piperazin-1-yl]-2-hydroxybutoxy}naphthalene, or a pharmaceutically acceptable salt or solvate thereof, (2S)-anti-1-{4-[4-(10,11-difluorocyclopropyldibenzosuber-5-yl)piperazin-1-yl]-2-hydroxybutoxy}phenanthrene, or a pharmaceutically acceptable salt or solvate thereof, (2S)-anti-1-{4-[4-(10,11-difluorocyclopropyldibenzosuber-5-yl)piperazin-1-yl]-2-hydroxybutoxy}anthracene, or a pharmaceutically acceptable salt or solvate thereof, (2S)-anti-1-{4-[4-(10,11-difluorocyclopropyldibenzosuber-5-yl)piperazin-1-yl]-2-hydroxybutoxy}triphenylene, or a pharmaceutically acceptable salt or solvate thereof, (2S)-anti-1-{4-[4-(10,11-difluorocyclopropyldibenzosuber-5-yl)piperazin-1-yl]-2-hydroxybutoxy}chrysene, or a pharmaceutically acceptable salt or solvate thereof, (2S)-anti-1-{4-[4-(10,11-difluorocyclopropyldibenzosuber-5-yl)piperazin-1-yl]-3-hydroxybutoxy}naphthalene, or a pharmaceutically acceptable salt or solvate thereof, (2S)-anti-1-{4-[4-(10,11-difluorocyclopropyldibenzosuber-5-yl)piperazin-1-yl]-3-hydroxybutoxy}phenanthrene, or a pharmaceutically acceptable salt or solvate thereof, (2S)-anti-1-{4-[4-(10,11-difluorocyclopropyldibenzosuber-5-yl)piperazin-1-yl]-3-hydroxybutoxy}anthracene, or a pharmaceutically acceptable salt or solvate thereof, (2S)-anti-1-{4-[4-(10,11-difluorocyclopropyldibenzosuber-5-yl)piperazin-1-yl]-3-hydroxybutoxy}triphenylene, or a pharmaceutically acceptable salt or solvate thereof, (2S)-anti-1-{4-[4-(10,11-difluorocyclopropyldibenzosuber-5-yl)piperazin-1-yl]-3-hydroxybutoxy}chrysene, or a pharmaceutically acceptable salt or solvate thereof, (2S)-anti-1-{3-[4-(10,11-cyclopropyldibenzosuber-5-yl)piperazin-1-yl]-2-hydroxypropoxy}naphthalene, or a pharmaceutically acceptable salt or solvate thereof, (2S)-anti-1-{3-[4-(10,11-cyclopropyldibenzosuber-5-yl)piperazin-1-yl]-2-hydroxypropoxy}phenanthrene, or a pharmaceutically acceptable salt or solvate thereof, (2S)-anti-1-{3-[4-(10,11-cyclopropyldibenzosuber-5-yl)piperazin-1-yl]-2-hydroxypropoxy}anthracene, or a pharmaceutically acceptable salt or solvate thereof, (2S)-anti-1-{3-[4-(10,11-cyclopropyldibenzosuber-5-yl)piperazin-1-yl]-2-hydroxypropoxy}triphenylene, or a pharmaceutically acceptable salt or solvate thereof, (2S)-anti-1-{3-[4-(10,11-cyclopropyldibenzosuber-5-yl)piperazin-1-yl]-2-hydroxypropoxy}chrysene, or a pharmaceutically acceptable salt or solvate thereof, (2S)-anti-1-{3-[4-(10,11-fluorocyclopropyldibenzosuber-5-yl)piperazin-1-yl]-2-hydroxypropoxy}naphthalene, or a pharmaceutically acceptable salt or solvate thereof, (2S)-anti-1-{3-[4-(10,11-fluorocyclopropyldibenzosuber-5-yl)piperazin-1-yl]-2-hydroxypropoxy}phenanthrene, or a pharmaceutically acceptable salt or solvate thereof, (2S)-anti-1-{3-[4-(10,11-fluorocyclopropyldibenzosuber-5-yl)piperazin-1-yl]-2-hydroxypropoxy}anthracene, or a pharmaceutically acceptable salt or solvate thereof, (2S)-anti-1-{3-[4-(10,11-fluorocyclopropyldibenzosuber-5-yl)piperazin-1-yl]-2-hydroxypropoxy}triphenylene, or a pharmaceutically acceptable salt or solvate thereof, (2S)-anti-1-{3-[4-(10,11-fluorocyclopropyldibenzosuber-5-yl)piperazin-1-yl]-2-hydroxypropoxy}chrysene, or a pharmaceutically acceptable salt or solvate thereof, (2S)-anti-2-{3-[4-(10,11-difluorocyclopropyldibenzosuber-5-yl)piperazin-1-yl]-2-hydroxypropoxy}naphthalene, or a pharmaceutically acceptable salt or solvate thereof, (2S)-anti-2-{3-[4-(10,11-difluorocyclopropyldibenzosuber-5-yl)piperazin-1-yl]-2-hydroxypropoxy}phenanthrene, or a pharmaceutically acceptable salt or solvate thereof, (2S)-anti-2-{3-[4-(10,11-difluorocyclopropyldibenzosuber-5-yl)piperazin-1-yl]-2-hydroxypropoxy}anthracene, or a pharmaceutically acceptable salt or solvate thereof, (2S)-anti-2-{3-[4-(10,11-difluorocyclopropyldibenzosuber-5-yl)piperazin-1-yl]-2-hydroxypropoxy}triphenylene, or a pharmaceutically acceptable salt or solvate thereof, (2S)-anti-2-{3-[4-(10,11-difluorocyclopropyldibenzosuber-5-yl)piperazin-1-yl]-2-hydroxypropoxy}chrysene, or a pharmaceutically acceptable salt or solvate thereof, and mixtures thereof.

A more preferred compound of the invention is (2R)-anti-1-{3-[4-(10,11-difluorocyclopropyldibenzosuber-5-yl)piperazin-1-yl]-2-hydroxypropoxy}naphthalene, or pharmaceutically acceptable salts or solvates thereof. This more preferred compound is illustrated in Formula (AI):

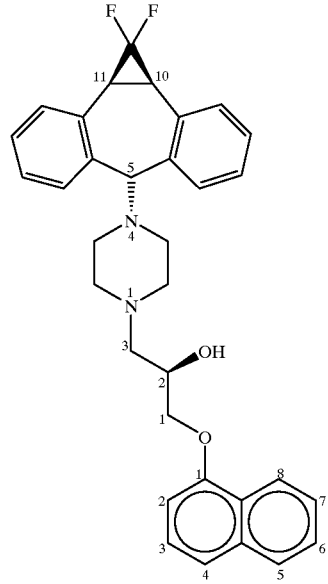

Formula (AI)

Generally, the compounds of Formula (A) are prepared by following the procedures described in PCT Patent Application PCT/US94/04215 and U.S. Pat. No. 5,112,817, both incorporated herein by reference. The compounds of Formula (A) are prepared by incorporating a 10,11-cyclopropyldibenzosuberone (optionally including non-hydrogen substituents at the $R^1$ and $R^2$ positions) in place of the dibenzosuberone. The 10,11-cyclopropyldibenzosuberone can be prepared, for example, as described in "Imine Analogues of Tricyclic Antidepressants," by Ciganek, et al., *J.Med.Chem.*, 1981, 24, 336–41; or in "Aminoalkyldibenzo[a,e]cyclopropa[c]-cycloheptene Derivatives. A Series of Potent Antidepressants," by Coyne and Cusic, *J.Med.Chem.*, 1974, Vol. 17, No. 1, 72–75.

To make the compounds of Formula (A) the aryl alcohol used to make the $R^3$ component of Formula (A) must be a polyaryl (two to four fused aromatic carbocyclic ring) alcohol. The polyaryl alcohol is reacted as described in PCT Patent Application PCT/US94/04215 (Page 13, lines 35–44) and U.S. Pat. No. 5,112,817 (Column 15, lines 21–52) with a compound selected from a group that may include a nosyl (such as 3-nitrophenyl-sulfonyl-glycidal) derivative as well as a tosyl or mesyl derivative of 1-chloro-2,3-epoxybutane, 1-bromo-2,3-epoxy-butane, epibromohydrin or epichlorohydrin.

Isolation and purification of the compounds and intermediates can be effected, if desired, by any suitable separation or purification procedure such as, for example, filtration, extraction, crystallization, column chromatography, thin-layer chromatography or thick-layer chromatography, or a combination of these procedures.

The compounds of Formula (A) can be converted to corresponding acid addition salts. The conversion is accomplished by treatment with a stoichiometric amount of an appropriate acid, which appropriate acid includes inorganic acids, such as hydrochloric acid, hydrobromic acid, sulfuric acid (giving the sulfate and bisulfate as acetic salts), nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, salicylic acid, p-toluene-sulfonic acid, hexanoic acid, heptanoic acid, cyclopentanepropionic acid, lactic acid, o-(4-hydroxy-benzoyl)benzoic acid, 1,2-ethanedisulfonic acid, 2-hydroxyethanesulfonic acid, benzenesulfonic acid, p-chlorobenzenesulfonic acid, 2-naphthalenesulfonic acid, camphorsulfonic acid, 4-methylbicyclo[2.2.2]oct-2-ene-1-carboxylic acid, glucoheptonic acid, 4,4'-methylenebis(3-hydroxy-2-naphthoic) acid, 3-phenylpropionic acid, trimethylacetic acid, t-butylacetic acid, laurylsulfuric acid, glucuronic acid, glutamic acid, 3-hydroxy-2-naphthoic acid, stearic acid, muconic acid and the like. In the salt-forming step of this invention, the free base is typically dissolved in a polar organic solvent, such as methanol or ethanol, and the acid is added in water, methanol or ethanol. The temperature is maintained at 0° C. to 50° C. The corresponding salt precipitates spontaneously or can be brought out of solution with a less polar solvent, or by evaporation of the solvent or by cooling the solution.

In the step of liberating the free base of Formula (A) according to the invention the acid addition salts of the compounds of Formula (A) can be decomposed to the corresponding free bases by treatment with an excess of a suitable base, such as ammonia or sodium bicarbonate, typically in the presence of an aqueous solvent, and at a temperature between 0° C. and 50° C. The free base is isolated by conventional means, such as extraction with an organic solvent. The stoichiometric excess must take into account the number of equivalents of acid bound by the base of Formula (A).

As stated above, the present invention includes solvates of the compounds of Formula (A) and the pharmaceutically acceptable salts therein. A particular compound of the present invention or a pharmaceutically acceptable salt thereof may form solvates with water or common organic solvents. Such solvates are included within the scope of compounds of the present invention.

Utility

The compounds of the present invention are useful as drug and multidrug resistance modulators. They are useful for treating drug and multidrug resistance after resistance becomes clinically evident, and can also be administered at the time of initial drug therapy, before any clinical resistance becomes evident, to enhance the activity of drugs from the beginning of drug administration.

The compounds of the present invention are particularly useful for the treatment of drug resistant and multidrug resistant cancer and drug resistant malaria.

The compounds of the present invention are also useful for enhancing the oral bioavailability of a drug.

The compounds of the present invention are also useful for enhancing bioavailability of a drug to the brain.

As stated above, the present invention includes mixtures of the compounds or pharmaceutically acceptable salts or solvates of Formula (A). Preferred mixtures consist of racemic mixtures containing at least one pair of enantiomers. A preferred mixture is a racemic mixture of the 2R and 2S enantiomers of anti-1-{3-[4-(10,11-difluorocyclopropyl-dibenzosuber-5-yl)piperazin-1-yl]-2-hydroxypropoxy}-naphthalene.

In Vitro Testing for Multidrug Resistance Modulation with Cancer Chemotherapeutic Drugs Compounds are evaluated for their ability to show multidrug resistance modulation when coadministered with an oncolytic. Cell cytotoxicity assays are conducted by growing a P-glycoprotein-expressing multidrug resistant cell line such as CEM/VLB$_{100}$ (available from, among others, Dr. William Beck of St. Jude's Research Hospital in Tennessee), P388 VCR (available through DCT Repository, NCI, Frederick, Md.) and CHCR5 (available from, among others, Dr. Victor Ling, Vancouver, B.C. Cancer Agency, Vancouver, B.C.) in the presence of an appropriate oncolytic and the multidrug resistance modulator as described below.

MTT, {3-(4,5-dimethyl-thiazol-2-yl)-2,5-diphenyl tetrazolium bromide], DOX (doxorubicin), VP-16 (etoposide) and VLB (vinblastine sulfate) can be obtained from Sigma Chemical Co. (St. Louis, Mo.). Taxol® can be obtained from ICN Biomedicals, Inc. (Costa Mesa, Calif.). FBS (fetal bovine serum) can be purchased from Hyclone (Logan, Utah). L-glutamine and Minimum Essential Media for suspension cultures (SMEM) can be purchased from GIBCO (Grand Island, N.Y.). Tissue culture Seroclusters 96-well with round bottom wells can be obtained from Costar (Cambridge, Mass.). Tissue culture flask can be obtained from Corning Glass Works (Corning, N.Y.).

The human leukemia cell lines parental CCRF-CEM and the multidrug resistant CEM/VLB$_{100}$ (selected with 100 ng/ml vinblastine) can be provided by William T. Beck (Beck, W. T., Mueller, M. J., and Tanzer L. R., Altered Surface Membrane Glycoproteins in Vinca Alkaloid—Resistant Human Leukemic Lymphoblast, *Cancer Research*, 39, 2070–2076 (1979)). The cells can be maintained in SMEM medium supplemented with 10% FBS and 2 mM L-glutamine in a humidified incubator with 95% air and 5% $CO_2$. Cell number can be determined using a Coulter Counter model ZM. Cells can be subcultured every 3–4 days.

Cell viability can be determined using a modified MTT dye reduction method (Denziot, F., Lang, R., Rapid colorimetric assay for cell growth and survival modifications to the tetrazolium procedure giving improved sensitivity and reliability, *J. Immunological Methods*, 89, 271–277, (1986)), as described:

Cells are harvested during the logarithmic growth phase, and seeded in 96-well serocluster plates at 7.5×10³ cells/well and cultured for 72 hours in the presence of serially diluted oncolytics (VLB, DOX, VP-16 and Taxol®) ± modulators. A single well assay is conducted using a fixed concentration of VLB (4 ng/ml) and modulator (5 μM). The cytotoxicity of the modulator alone, at the same concentration is also determined. Modulators are prepared as 2 mM stocks in DMSO and added to the wells to give final concentrations ranging from 5 μM to 0.5 μM. After 72 hours, 20 μl of freshly prepared MTT (5 mg/ml in Dulbecco's phosphate buffered saline pH 7.5) is added to each well and placed for 4 hours in a 37° C. incubator. Cells are pelleted at 1800 R.P.M. for 10 minutes in a Sorvall RT6000B centrifuge. After centrifugation, 70 μl of medium is carefully removed from each well, and 100 μl of 2-propanol/0.04 N HCl is added to dissolve the blue formazan stained cells. Cells are resuspended 5–10 times with a multipipettor or until no particulate matter was visible. Plates are immediately read on a Yitertek MCC/340 microplate reader (Flow Laboratories (McLean, Va.) with a wavelength of 570 nm and a reference wavelength of 630 nm). Controls are measured in quadruplicate and modulators in duplicate.

$IC_{50}$'s are calculated from semilog dose response curves in the presence and absence of modulators for both the parent and resistant cell lines. The fold shift is calculated as the $IC_{50}$ for cells treated with oncolytic alone divided by the $IC_{50}$ for cells treated with oncolytic + modulator.

Taxol® was chosen as the test oncolytic for the studies reported herein due to the high level of resistance of the cell line CEM/VLB$_{100}$ to taxol. The $IC_{50}$ of Taxol® is determined in the presence of varying concentrations of the modifier, with the goal of achieving full reversal activity. Full reversal activity, or 100% reversal activity, is defined as the ability to achieve drug sensitivity in the multidrug resistant cell line which is equivalent to the sensitivity of the drug sensitive parental cell line. This data is presented here as $Rev_{50}$ and $Rev_{100}$. These numbers are defined as the lowest concentration of modifier (in $\mu M$) which can achieve 50% and 100% reversal activity, respectively.

In Vitro Testing for Drug Resistance Modulation of Anti-Malarial Drugs used in the Treatment of Drug Resistant Malaria Compounds are evaluated for their ability to exhibit drug resistance modulation when coadministered with an anti-malarial drug used in the treatment of drug resistant malaria. The tests are conducted by placing the drug resistance modulator in the drug resistant malaria species in the presence of an anti-malarial drug. The anti-malarial drug is a drug that the drug resistant malaria species is known to be resistant to. For example, the malaria species *P. lophurae* and *P. cynumolgi* are both resistant to the anti-malarial drug proguanil. Modulator activity is defined as the ability to achieve drug sensitivity to the anti-malarial drug in the drug resistant malaria species by coadministration of the anti-malarial drug and the drug resistance modulator of choice.

Further details on testing for reversal of drug resistance in various malaria species can be found in standard references about malaria, such as: *Chemotheraphy of Malaria*, by Covell, et al., ©1955 by World Health Organization, Geneva, and *Practical Malariology*, 2nd Edition, by Russell et al., ©1963 by Oxford University Press.

Testing for Oral Bioavailability of a Compound

A simple test to determine oral bioavailability of a drug is to administer the drug orally and then test for the presence of the drug, or its metabolites, in the blood using standard blood analytical techniques. The test is run twice, once with the drug administered by itself and the second time the drug is administered in the presence of a drug resistance modulator. The results are compared to see how much more compound is orally bioavailable when the modulator is present.

Testing for Bioavailability of a Drug to the Brain by Testing for Movement of the Compound Across the Blood-Brain Barrier An in vitro test for movement of a compound across the blood-brain barrier is begun by growing a confluent monolayer of either bovine brain endothelial or mouse brain capillary endothelial cells on a porous filter support to form a tight endothelium cell layer. The filter support is placed in a vessel containing phosphate buffered saline such that the only way for materials to get from one side of the vessel to another is through the cell layer/porous filter support.

A known compound (e.g. mannitol) is placed in the vessel on the serosal side of the cell layer/porous filter. Samples are removed from the non-serosal side of the cell layer/porous filter at 15–30 minute intervals over a 3–6 hour time period. Standard analytical techniques are used to determine the amount of known compound in the sample. This information is used to calculate the base line permeability of the cell layer/porous filter.

The drug of interest (e.g., oncolytic or anti-malarial) is then placed on one side of a vessel containing fresh saline and the same type of cell layer/porous filter barrier. Samples are removed from the other side at 15–30 minute intervals over a 3–6 hour time period. Standard analytical techniques are used to determine the amount of drug of interest in those samples. The amount of drug of interest that migrates across the barrier is indicative of the base line permeability of the cell layer/porous filter for that drug.

The test is then repeated, only this time the drug of interest and a drug resistance modulator are both placed on one side of a vessel prepared as before. Samples are pulled and tests are run as described above to see how much more of the drug of interest migrates across the cell layer/porous filter support with the drug resistance modulator being present.

An in vivo test to determine whether a drug administered to a mammal has crossed the blood brain barrier is to administer the drug to the mammal in any acceptable manner and then test for the presence of the drug, or its metabolites, in the mammal's cerebrospinal fluid.

The compounds of the present invention may be administered to any mammal. Of all mammals, it is believed that humans will benefit the most from administration of these compounds.

The compounds of Formula (A) are administered at a therapeutically effective dosage, e.g., a dosage sufficient for the compound to:

(i) act as a drug or multidrug resistance modulator when coadministered with a treatment drug for a drug or multidrug resistant disease;

(ii) enhance the oral bioavailability of a drug; and/or (iii) enhance the bioavailability of a drug to the brain.

Treatment of a disease includes:

(i) preventing the disease, that is, causing the clinical symptoms of the disease not to develop;

(ii) inhibiting the disease, that is, arresting the development of clinical symptoms; and/or (iii) relieving the disease, that is, causing the regression of clinical symptoms.

The compounds of Formula (A) are typically co-administered either before, during or after the administration of a drug that treats the disease in question. A preferred administration schedule is a continuous infusion over the 24 hour period during which the treatment drug is also administered. For cancer, a treatment drug would be a cancer chemotherapeutic agent, including, but not limited to, paclitaxel, doxorubicin, adriamycin, etoposide, teniposide, vinblastine, vincristine, mitomycin C, daunorubicin, and teniposide. For malaria a treatment drug would be an anti-malarial treatment drug, including but not limited to, pamaquine, primaquine, mepacrine, doxycycline, chloroquine, amodiaquine, quinine, quinidine, pyrimethamine, proguanil, mefloquine and sulphadiazine.

A daily dose of drug or multidrug resistance modulator for all methods of treatment described herein is from about 100 mg/M$^2$ of body surface area to about 1 g/M$^2$ of body surface area, preferably from about 200 mg/M$^2$ to about 800 mg/M$^2$ of body surface area and most preferably from about 400 mg/M² to about 500 mg/M² of body surface area. The amount of drug or multidrug resistance modulator compound administered will, of course, be dependent on the patient and the disease state being treated, the severity of the affliction, the manner and schedule of administration (e.g., oral administration one day prior to cancer chemotherapy as compared to intravenous administration during cancer chemotherapy) and the judgment of the prescribing physician.

The dosage level of the disease treatment drug is adjusted for each recipient to maximize the efficacy of the disease treatment drug while minimizing any undesirable side effects. When a drug or multidrug resistance modulator is coadministered with a disease treatment drug, the dosage of the disease treatment drug may stay the same or be decreased, depending upon the efficacy of the drug or multidrug resistance modulator in performing its function.

In employing the compounds of this invention for treatment of drug or multidrug resistance, any pharmaceutically acceptable mode of administration can be used. The compounds of Formula (A) can be administered either alone or in combination with other pharmaceutically acceptable excipients. These include solid, semi-solid and liquid dosage forms, such as, for example, tablets, capsules, powders, liquids, suspensions, suppositories or the like. The compounds of Formula (A) can also be administered in sustained or controlled release dosage forms, including depot injections, osmotic pumps, pills, transdermal (including electrotransport) patches, and the like, for the prolonged administration of the compound at a predetermined rate, preferably in unit dosage forms suitable for single administration of precise dosages. The compositions will typically include a conventional pharmaceutical carrier, diluent or excipient and a compound of Formula (A) or a pharmaceutically acceptable salt thereof. In addition, these compositions may include other medicinal agents, pharmaceutical agents, carriers, adjuvants, etc., such as the cancer chemotherapeutic agents listed above.

Generally, depending on the intended mode of administration, the pharmaceutically acceptable composition will contain from about 0.005% to about 95%, preferably from about 0.5% to about 50%, by weight of a compound or salt or solvate of Formula (A), the remainder being suitable pharmaceutical excipients, carriers and diluents.

One manner of administration for the conditions detailed above is oral, using a convenient daily dosage regimen which can be adjusted according to the degree of affliction. For such oral administration, a pharmaceutically acceptable, non-toxic composition is formed by the incorporation of any of the normally employed excipients, such as, for example, mannitol, lactose, starch, magnesium stearate, sodium saccharine, talcum, cellulose, sodium crosscarmellose, glucose, gelatin, sucrose, magnesium carbonate, and the like. Such compositions include solutions, suspensions, tablets, dispersible tablets, pills, capsules, powders, sustained release formulations and the like.

Preferably the oral compositions will take the form of a pill or tablet. Thus, the composition will contain along with the active ingredient: a diluent such as lactose, sucrose, dicalcium phosphate, or the like; a lubricant such as magnesium stearate or the like; and a binder such as starch, gum acacia, gelatin, polyvinylpyrrolidone, cellulose and derivatives thereof, and the like.

Liquid pharmaceutically administrable compositions can, for example, be prepared by dissolving, dispersing, etc., an active compound as defined above and optional pharmaceutical adjuvants in a carrier, such as, for example, water, saline, mannitol, aqueous dextrose, glycerol, glycol, ethanol and the like, to thereby form a solution or suspension. If desired, the pharmaceutical composition to be administered may also contain minor amounts of non toxic auxiliary substances such as wetting agents, emulsifying agents, or solubilizing agents, pH buffering agents and the like, for example, acetate, sodium citrate, cyclodextrine derivatives, sorbitan monolaurate, triethanolamine sodium acetate, triethanolamine oleate, etc. Actual methods of preparing such dosage forms are known, or will be apparent, to those skilled in this art; for example, see Remington's Pharmaceutical Sciences, Mack Publishing Company, Easton, Pa., 19th Edition, 1995.

Parenteral administration is generally characterized by injection (e.g. subcutaneously, intramuscularly, intravenously) or infusion through a central line. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol, mannitol or the like. In addition, if desired, the pharmaceutical compositions to be administered may also contain minor amounts of non-toxic auxiliary substances such as wetting or emulsifying agents, pH buffering agents, solubility enhancers, and the like, such as for example, sodium acetate, sorbitan monolaurate, triethanolamine oleate, cyclodextrins, etc. A preferred liquid solution for parenteral administration contains an appropriate amount of compound in a 5% solution of mannitol in water.

A more recently devised approach for parenteral administration employs the implantation of a slow-release or sustained-release system, such that a constant level of dosage is maintained. See, e.g., U.S. Pat. No. 3,710,795.

The percentage of active compound contained in such parenteral compositions is highly dependent on the specific nature thereof, as well as the activity of the compound and the needs of the subject. However, percentages of active ingredient of from about 0.01% to about 10% in solution are employable, and will be higher if the composition is a solid which will be subsequently diluted to the above percentages. Preferably, the parenteral composition will contain from about 0.2% to about 2% of the active agent in solution.

The preferred manner of administering the active compound is, at the present time, infusion through a central line.

EXAMPLES

The following preparations and examples are given to enable those skilled in the art to more clearly understand and to practice the present invention. They should not be considered as limiting the scope of the invention, but merely as being illustrative and representative thereof.

Example 1

A) (S)1-(1-Naphthyloxy)-2,3-epoxypropane

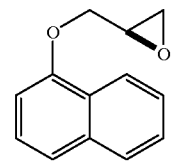

(i)

To a suspension of 48 mg (1.20 mmol) of sodium hydride (60% in mineral oil) in 3 mL of DMF were added 173 mg (1.20 mmol) of 1-naphthol while stirring at 0° C. The reaction was allowed to warm to 25° C. and stirred an additional 1 hour. The reaction was recooled to 0° C., and a solution of 260 mg (1.0 mmol) of (S)-(−)-(3-nitrophenylsulfonyl)-glycidol in 1 mL of DMF was added dropwise. The reaction was stirred at 0° C. for 2 hours, poured into 25 mL of brine and the product extracted into ethyl acetate (5×). The combined organic extracts were dried over sodium sulfate and concentrated in vacuo to give 240 mg of the compound of Formula (i) (S) 1-(1-Naphthyloxy)-2,3-epoxypropane, which was used without further purification.

B) (2R)-anti-1-{3-[4-(10,11-difluorocyclopropyldibenzosuber-5-yl)piperazin-1-yl]-2-hydroxypropoxy}naphthalene

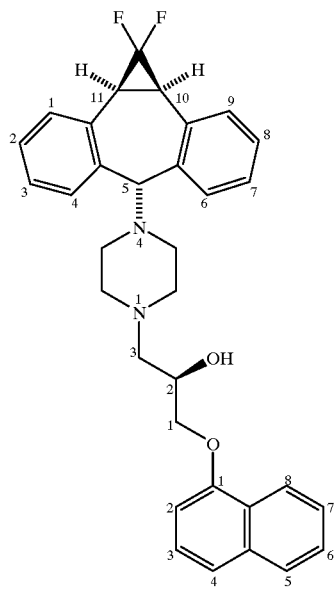

(AI)

A solution containing 50 mg (0.25 mmol) of 4'-H-1'-(10,11-difluorocyclopropyldibenzosubarane)piperazine and 84 mg (0.26 mmol) of (S) 1-(1-Naphthyloxy)-2,3-epoxypropane (i) in 2 mL of isopropanol was heated at reflux for 18 hours. The reaction was cooled to 25° C. and concentrated in vacuo. This crude material was purified by flash chromatography on a silica gel column using 2% methanol-methylene chloride as the eluent. The major fraction was collected and concentrated in vacuo to give 150 mg of a white amorphous solid. A name for the structure of Formula (AI) is (2R)-anti-1-{3-[4-(10,11-difluorocyclopropyldibenzosuber-5-yl)piperazin-1-yl]-2-hydroxypropoxy}naphthalene. mp (free base)=84–90° C.

In vitro testing of this compound on the P-glycoprotein expressing cell line CEM/VLB$_{100}$ for multidrug resistance with the cancer chemotherapeutic drug Taxol® showed a Rev$_{100}$ ($\mu$M) of 1.0 and a Rev$_{50}$ ($\mu$M) of 0.70.

The following formulation examples are illustrative only and are not intended to limit the scope of the invention in any way. "Active ingredient" means a compound of Formula (A) or a pharmaceutically acceptable salt or solvate thereof.

Formulation 1

Hard gelatin capsules are prepared using the following ingredients:

|  | Quantity (mg/capsule) |
| --- | --- |
| Active ingredient | 250 |
| Starch, dried | 200 |
| Magnesium stearate | 10 |
| Total | 460 mg |

Formulation 2

A tablet is prepared using the ingredients below:

|  | Quantity (mg/capsule) |
| --- | --- |
| Active ingredient | 250 |
| Cellulose, micro crystalline | 400 |
| Silicon dioxide, fumed | 10 |
| Stearic acid | 5 |
| Total | 665 mg |

The components are blended and compressed to form tablets each weighing 665 mg.

Formulation 3

Tablets, each containing 60 mg of active ingredient, are made as follows:

|  | Quantity (mg/tablet) |
| --- | --- |
| Active ingredient | 60 |
| Starch | 45 |
| Micro crystalline cellulose | 35 |
| Polyvinylpyrrolidone (as 10% solution in water) | 4 |
| Sodium carboxymethyl starch | 4.5 |
| Magnesium stearate | 0.5 |
| Talc | 1 |
| Total | 150 |

The active ingredient, starch and cellulose are passed through a No. 45 mesh U.S. sieve and mixed thoroughly. The aqueous solution containing polyvinylpyrrolidone is mixed with the resultant powder, and the mixture then is passed through a No. 14 mesh U.S. sieve. The granules so produced are dried at 50° C. and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

Formulation 4

Capsules, each containing 80 mg of active ingredient, are made as follows:

|  | Quantity (mg/capsule) |
| --- | --- |
| Active ingredient | 80 |
| Starch | 59 |
| Micro crystalline cellulose | 59 |
| Magnesium stearate | 2 |
| Total | 200 |

The active ingredient, cellulose, starch, and magnesium stearate are blended, passed through a No. 45 mesh U.S. sieve, and filled into hard gelatin capsules in 200 mg quantities.

Formulation 5

Suppositories, each containing 225 mg of active ingredient, are made as follows:

|  | Quantity (mg/unit) |
| --- | --- |
| Active ingredient | 225 |
| Saturated fatty acid glycerides | 2,000 |
| Total | 2,225 |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

Formulation 6

Suspensions, each containing 50 mg of active ingredient per 5 mL dose, are made as follows:

|  | Quantity |
| --- | --- |
| Active ingredient(s) | 50 mg |
| Sodium carboxymethyl cellulose | 50 mg |
| Syrup | 1.25 ml |
| Benzoic acid solution | 0.10 mL |
| Flavor | q.v. |
| Color | q.v. |
| Purified water to total | 5 mL |

The active ingredient is passed through a No. 45 mesh U.S. sieve and mixed with the sodium carboxymethyl cellulose and syrup to form a smooth paste. The benzoic acid solution, flavor and color are diluted with a portion of the water and added, with stirring. Sufficient water is then added to produce the required volume.

Formulation 7

An intravenous formulation may be prepared as follows:

|  | Quantity |
| --- | --- |
| Active ingredient | 100 mg |
| Isotonic saline | 1,000 mL |

What is claimed is:

1. A compound of Formula (A):

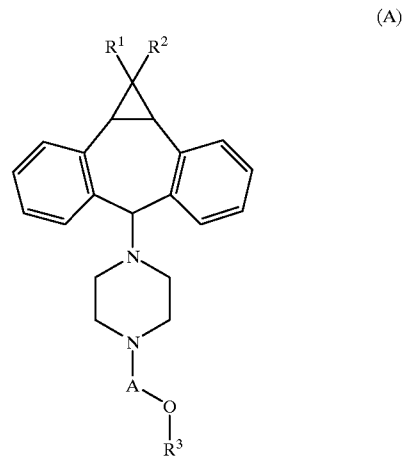

(A)

where $R^1$ and $R^2$ are independently hydrogen or halo; A is —CH$_2$—CH$_2$—, —CH$_2$—CHR$^4$—CH$_2$—, or —CH$_2$—CHR$^5$—CHR$^6$—CH$_2$—, where $R^4$ is —H, —OH, or acyloxy; one of $R^5$ and $R^6$ is —H, —OH or acyloxy, and the other is —H; and $R^3$ is naphthalene; and pharmaceutically acceptable salts or hydrates thereof.

2. A compound of claim 1 selected from the group consisting of
(2R)-anti-1-{3-[4-(10,11-difluorocyclopropyldibenzosuber-5-yl)piperazin-1-yl]-2-hydroxypropoxy}naphthalene, or a pharmaceutically acceptable salt or hydrate thereof,
(2R)-syn-1-{3-[4-(10,11-difluorocyclopropyldibenzosuber-5-yl)piperazin-1-yl]-2-hydroxypropoxy}naphthalene, or a pharmaceutically acceptable salt or hydrate thereof,
(2R)-anti-1-{4-[4-(10,11-difluorocyclopropyldibenzosuber-5-yl)piperazin-1-yl]-2-hydroxybutoxy}naphthalene, or a pharmaceutically acceptable salt or hydrate thereof,
(2R)-anti-1-{4-[4-(10,11-difluorocyclopropyldibenzosuber-5-yl)piperazin-1-yl]-3-hydroxybutoxy}naphthalene, or a pharmaceutically acceptable salt or hydrate thereof,
(2R)-anti-1-{3-[4-(10,11-cyclopropyldibenzosuber-5-yl)piperazin-1-yl]-2-hydroxypropoxy}naphthalene, or a pharmaceutically acceptable salt or hydrate thereof,
(2R)-anti-1-{3-[4-(10,11-fluorocyclopropyldibenzosuber-5-yl)piperazin-1-yl]-2-hydroxypropoxy}naphthalene, or a pharmaceutically acceptable salt or hydrate thereof,
anti-1-{2-[4-(10,11-cyclopropyldibenzosuber-5-yl)piperazin-1-yl]ethoxy}naphthalene, or a pharmaceutically acceptable salt or hydrate thereof,
(2R)-anti-2-{3-[4-(10,11-difluorocyclopropyldibenzosuber-5-yl)piperazin-1-yl]-2-hydroxypropoxy}naphthalene, or a pharmaceutically acceptable salt or hydrate thereof,
(2S)-anti-1-{3-[4-(10,11-difluorocyclopropyldibenzosuber-5-yl)piperazin-1-yl]-2-hydroxypropoxy}naphthalene, or a pharmaceutically acceptable salt or hydrate thereof, (2S)-anti-1-{4-[4-(10,11-difluorocyclopropyldibenzosuber-5-yl)piperazin-1-yl]-2-hydroxybutoxy}naphthalene, or a pharmaceutically acceptable salt or hydrate thereof, (2S)-anti-1-{4-[4-(10,11-difluorocyclopropyldibenzosuber-5-yl)piperazin-1-yl]-3-hydroxybutoxy}naphthalene, or a pharmaceutically acceptable salt or hydrate thereof, (2S)-anti-1-{3-[4-(10,11-cyclopropyldibenzosuber-5-yl)piperazin-1-yl]-2-hydroxypropoxy}naphthalene, or a pharmaceutically acceptable salt or hydrate thereof, (2S)-anti-1-{3-[4-(10,11-fluorocyclopropyldibenzosuber-5-yl)piperazin-1-yl]-2-hydroxypropoxy}naphthalene, or a pharmaceutically acceptable salt or hydrate thereof, (2S)-anti-2-{3-[4-(10,11-difluorocyclopropyldibenzosuber-5-yl)piperazin-1-yl]-2-hydroxypropoxy}naphthalene, or a pharmaceutically acceptable salt or hydrate thereof; and mixtures thereof.

3. A compound of claim 1 which is:

(2R)-anti-1-{3-[4-(10,11-difluorocyclo-propyldibenzo-suber-5-yl)piperazin-1-yl]-2-hydroxypropoxy}-naphthyl, or a pharmaceutically acceptable salt or hydrate thereof.

4. A pharmaceutical composition comprising a compound or a salt or hydrate thereof of claim 1 in association with a pharmaceutically acceptable carrier, diluent, or excipient.

5. A method of treatment for a P-glycoprotein mediated drug resistant cancer comprising coadministering to a mammal in need thereof a resistance modulating amount of a compound or salt or hydrate thereof of claim 1 and an effective amount of a treatment drug for said drug resistant disease.

6. A method of treatment for a P-glycoprotein mediated multidrug resistant cancer comprising coadministering to a mammal in need thereof a multidrug resistance modulating amount of a compound or salt or hydrate thereof of claim 1 and an effective amount of a treatment drug for said multidrug resistant disease.

* * * * *

UNITED STATES PATENT AND TRADEMARK OFFICE
CERTIFICATE OF CORRECTION

PATENT NO.   : 6,025,359                                        Page 1 of 1
DATED         : February 15, 2000
INVENTOR(S)  : Julian Stanley Kroin, et al.

It is certified that error appears in the above-identified patent and that said Letters Patent is hereby corrected as shown below:

Column 20,
Line 36, please delete "napthalene" and insert --napthyl--.

Column 22,
Line 1, please delete napthyl" and insert --napthalene--.

Signed and Sealed this

Third Day of July, 2001

Attest:

NICHOLAS P. GODICI
Attesting Officer     Acting Director of the United States Patent and Trademark Office